United States Patent [19]
DeCamp et al.

[11] Patent Number: 5,338,875
[45] Date of Patent: Aug. 16, 1994

[54] BORON CONTAINING INTERMEDIATES USEFUL IN THE PREPARATION OF CARBAPENEMS

[75] Inventors: Ann DeCamp, Scotch Plains; Ulf H. Dolling, Westfield; Yulan Li, Edison; Dale L. Rieger, Westfield; Nobuyoshi Yasuda, Mountainside; Lyndon C. Xavier, Edison, all of N.J.

[73] Assignee: Merck & Co., Inc., Rahway, N.J.

[21] Appl. No.: 978,598

[22] Filed: Nov. 19, 1992

[51] Int. Cl.$^5$ .............................................. C07F 7/02
[52] U.S. Cl. ........................................ 556/402; 562/7
[58] Field of Search ............................ 502/7; 556/402

[56] References Cited

U.S. PATENT DOCUMENTS 3,038,926  6/1962  Farthouat ............................ 562/7
3,090,801  5/1963  Washburn et al. ................... 562/7

FOREIGN PATENT DOCUMENTS

0444889A1  9/1991  European Pat. Off. .

OTHER PUBLICATIONS

CA 16:3640 1922.
Chemistry Letters, pp. 1405–1408, 1989.
J. Am. Chem. Soc. 1985, 107, 972–980.
J. Med. Chem. 1987, 30, 871–880.
J. Org. Chem. 1990, 55, 5833–5847.
Synthetic Communications, 11(7), 513–519 (1981).
Synthetic Communications, 20(14), 2185–2189 (1990).
Tetrahedron Letters vol. 21, pp. 4221–4224.
Tetrahedron Letters vol. 29, No. 45, pp. 5739–5742, 1988.
Tetrahedron Letters vol. 29, No. 47, pp. 6043–6046, 1988.
Tetrahedron Letters vol. 31, No. 12, pp. 1665–1668, 1990.
Tetrahedron Letters vol 31, No. 20, pp. 2853–2856, 1990.
Tetrahedron Letters vol. 31, No. 23, pp. 3291–3294, 1990.
Tetrahedron Letters vol. 31, No. 24, pp. 3389–3392, 1990.

*Primary Examiner*—James H. Reamer
*Assistant Examiner*—Rebecca Cook
*Attorney, Agent, or Firm*—Richard C. Billups; Curt C. Panzer; Mark R. Daniel

[57] ABSTRACT

The present invention is directed to intermediates of the following formula which are useful in the preparation of Carbapenem-antibiotics

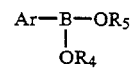

4 Claims, No Drawings

BORON CONTAINING INTERMEDIATES USEFUL IN THE PREPARATION OF CARBAPENEMS

BACKGROUND OF THE INVENTION

The invention disclosed herein concerns a process of making 2-aryl carbapenems. Carbapenem antibiotics, particularly thienamycin and imipenem (see U.S. Pat. Nos. 3,950,377 and 4,194,047) are well known for treating a broad spectrum of gram-negative and gram-positive bacterial infections. Active 2-Aryl substituted Carbapenem include those disclosed in U.S. Pat. Nos. 5,034,384 and 5,011,832.

As is generally appreciated by those with skill in the art, the Carbapenem nucleus is unstable, thus necessitating mild coupling reagents. The present methods of coupling utilize toxic reagents. For example, one alternative procedure utilizes highly toxic stannane reagents. The stannane procedure also introduces toxic impurities which made purification of the product and subsequent processing difficult.

Processes disclosed in the prior art include the following:

Coupling to produce 2-aryl carbapenems was previously performed via stannane chemistry (Rano et al. Tetrahedron Letters 1990, 2853). Related couplings with β-lactam containing substrates are given by Monroe and McDonald (Journal of Organic Chemistry 1989, 54, 5828), Kant (Tetrahedron Letters 1990, 3389), and Farina (Tetrahedron Letters 1988, 5739, 6043). Boronic acid or ester couplings were reported by Snieckus (Tetrahedron Letters 1990, 1665), Suzuki (Chem. Letters 1989, 1405; Journal of the American Chemical Society 1985, 107, 972).

In sharp contrast, the boronic acid coupling methodology disclosed herein present mild conditions, low toxicity and ease of product purification.

Selected examples of the generalized palladium catalyzed coupling of organometallic agents with enol triflates are reported by Scott and McMurry (Accounts of Chemical Research, 1988, 21,47), Stille (Agnew. Chem International Edition English, 1986, 25, 508) and Piers (Tetrahedron Letters 1991, 4555).

BRIEF DESCRIPTION OF THE INVENTION

The present invention is directed to a process of making 2-Aryl Carbapenems of formula 1 from a compound of Formula 2:

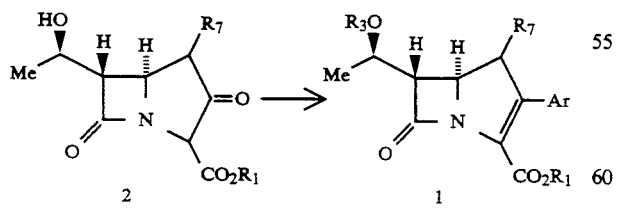

DETAILED DESCRIPTION OF THE INVENTION

In one embodiment, the invention concerns a process of making 2-aryl carbapenem intermediates of Formula 1,

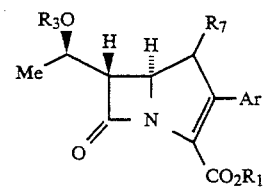

wherein
Ar is

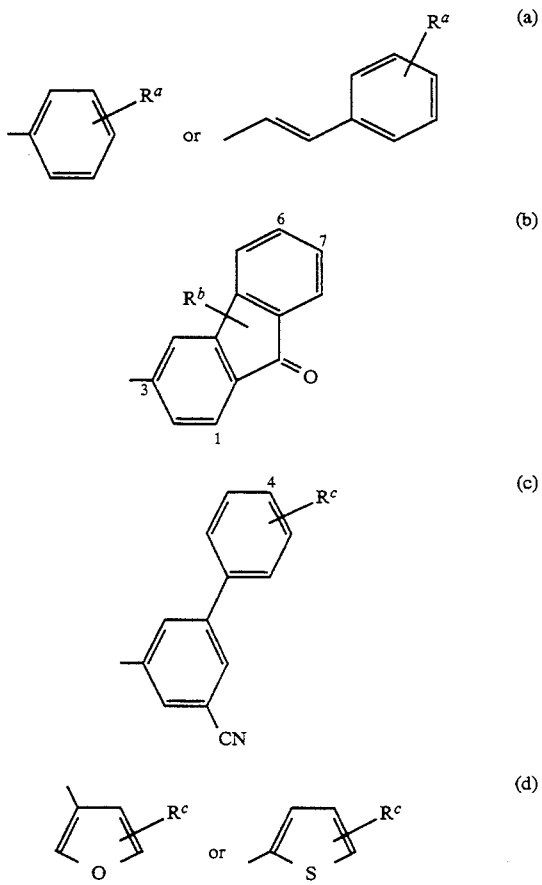

wherein
$R^a$ is
  (a) CN,
  (b) $CF_3$,
  (c) $C_{1-3}$ alkoxy,
  (d) $-NO_2$,
  (e) hydroxy $C_{1-3}$ alkyl, wherein the hydroxy is optionally protected with a silyl protecting group selected from tri-$C_{1-4}$ alkyl silyl, phenyl di $C_{1-4}$ alkyl and diphenyl mono $C_{1-4}$ alkyl silyl; or
  (f) substituted tetrazolyl wherein the substitutent is hydrogen, $C_{1-3}$alkyl, halo, hydroxy or $C_{1-3}$alkoxy;
$R^b$ is
  (a) $C_{1-3}$ alkyl,
  (b) $C_{1-3}$ alkoxy,
  (c) substituted $C_{1-3}$ alkyl, wherein the substituent is hydroxy, or
  (d) hydroxy $C_{1-3}$ alkyl, wherein the hydroxy is optionally protected with a silyl protecting group selected from tri-$C_{1-4}$ alkyl silyl, phenyl di $C_{1-4}$ alkyl and diphenyl mono $C_{1-4}$ alkyl silyl;

$R^c$ is
(a) $C_{1-3}$ alkyl,
(b) hydroxy $C_{1-3}$ alkyl, wherein the hydroxy is optionally protected with a silyl protecting group selected from tri-$C_{1-4}$ alkyl silyl, phenyl di $C_{1-4}$ alkyl and diphenyl mono $C_{1-4}$ alkyl silyl;

$R_1$ is a conventional protecting group, such as, but not limited to
(a) benzyl,
(b) p-methoxybenzyl,
(c) p-nitrobenzyl,
(d) o-nitrobenzyl,
(e) benzhydryl
(f) allyl,
(g) 2-trimethylsilylethyl or
(h) 2,2,2-trichloroethyl;

$R_3$ is
(a) hydrogen,
(b) a hydroxy protecting group selected from tri-$C_{1-4}$ alkyl silyl, phenyl di $C_{1-4}$ alkyl and diphenyl mono $C_{1-4}$ alkyl silyl;
(c) —C(O)OR'$_3$,
wherein R'$_3$ is
(a) benzyl,
(b) p-methoxybenzyl,
(c) p-nitrobenzyl,
(d) o-nitrobenzyl,
(e) benzhydryl
(f) allyl,
(g) 2-trimethylsilylethyl or
(h) 2,2,2-trichloroethyl;
(d) $CH_2 OR'_3$, or
(e) R'$_3$;

$R_7$ is hydrogen or methyl, including β-methyl;

(A) contacting a compound of Formula 2

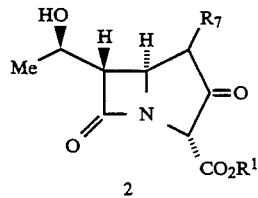

2 in a non-reactive solvent with an activating agent in the presence of a base to yield a compound of formula A;

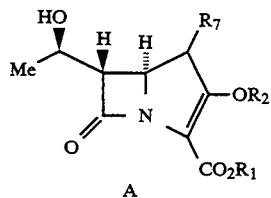

A wherein —$OR_2$ is a good leaving group such as
(a) triflate,
(b) fluorosulfonate,
(c) mesylate,
(d) tosylate,
(e) diaryl phosphate wherein the aryl group is mono or disubstituted phenyl and the substituents are each independently hydrogen or halo including chloro;

For purposes of this specification non-reactive solvents include halocarbon solvents such solvents as mono or di-halo $C_{1-4}$ alkyl including dichloromethane; etheral solvents such as diethyl ether di-n-butyl and diisopropyl ethers, cyclic ethers such as tetrahydropyran, and tetrahydrofuran; aromatic solvents such as benzene, toluene and xylene; and $C_{6-10}$ linear, branched or cyclic hydrocarbon solvent including hexane. Activating agents are defined to include bis-(3-chlorophenyl) chlorophosphate, diphenyl chlorophosphate, fluorosulfonic anhydride and trifluoromethanesulfonic anhydride, or others that will yield the substituent —$OR_2$. Suitable bases include but are not limited to pyrrole, pyridine, pyrrolidine, imidazole and lutidine, di $C_{1-3}$ alkylamine such as diisopropylamine and tri $C_{1-3}$ alkylamine such as triethylamine and diisopropyl ethylamine, metal amides, wherein metal is defined as sodium, potassium or lithium, including di-$C_{1-4}$ alkyl amides such as lithium diisopropylamide; $C_{1-4}$ alkyl metals such as n-butyllithium; metal $C_{1-4}$ alkoxides, such as potassium t-butoxide; metal hydrides such as sodium or potassium hydride; and metal carbonates sodium and potassium carbonates. The molar ratio of activating agent to Formula 2 should be approximately 0.90 to 1.0, but preferably not greater. A ratio of 0.95 is typical. The reaction may be conducted from approximately −20° C. to −80° C. preferably −70° C. to −80° C. The reaction is allowed to proceed until substantially complete in approximately 0.25–2 hours, typically 0.25–1.0 hours. The reaction is preferably conducted under nitrogen.

(B) Contacting the compound of formula A in non-reactive solvent as defined above, with a protecting agent suitable for removably protecting the hydroxyl of Formula 2 in the presence of a nitrogen containing base to yield a compound of Formula B;

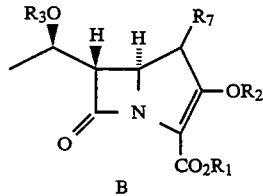

B wherein the protecting agent is $R_3X$, consisting of a protecting group $R_3$ and a good leaving group X.

For purposes of this specification, the protecting groups ($R_3$) suitable for step (B) include tri-organo silyl groups such as tri-$C_{1-3}$ alkyl silyl, including tri-methyl and tri-ethyl silyl and t-butyl di-methyl silyl. Also included is t-butyl di-phenylsilyl. Good leaving groups are defined to include chloro and triflate. Other suitable groups are found in Protective Groups in Organic Synthesis, Theodora W. Green, John Wiley and Sons 1981.

The nitrogen containing bases are defined as above. The molar ratio of compound A to the protecting agent should be approximately 1 to 1 or greater. The reaction should be allowed to proceed until complete and approximately 0.25 to 1.5 hours. The reaction may be conducted from −20° C. to −80° C. The reaction is preferably conducted under nitrogen.

As shown in the Example, preferably Step (B) is conducted in situ with the reaction mixture resulting from Step (A). Alternatively, Compound A can be isolated by standard means before continuing with the reaction scheme.

(C) Contacting the compound of Formula B and a coupling base in a coupling solvent with a compound of formula

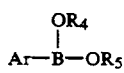

and a transition metal catalyst to yield a compound of Formula 1,

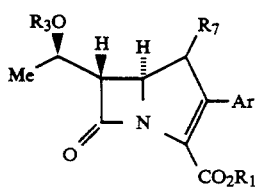

wherein $R_4$ and $R_5$ are each individually hydrogen or $C_{1-6}$ alkyl or $R_4$ and $R_5$ taken together are $C_{1-6}$ alkyl or $R_4$ and $R_5$ are joined together as to form

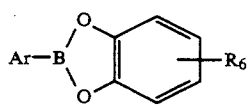

wherein $R_6$ is $C_{1-3}$ alkyl, halo, hydroxy, $C_{1-3}$ alkoxy or hydrogen.

For purposes of this specification coupling bases include but are not limited to metal hydroxides including barium, potassium, sodium, or lithium, thallium hydroxides; metal $C_{1-4}$ alkoxide such as sodium, potassium or lithium t-butoxide; and metal carbonate such as potassium or sodium carbonates. The coupling solvent is defined to include di-$C_{1-3}$ alkyl formamide such as dimethyl formamide, di-$C_{1-3}$ alkyl sulfoxide such as dimethylsulfoxide, N-methylpyrrolidinone, N-ethylpyrrolidinone.

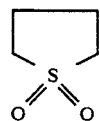

as well as halocarbon solvents such solvents as mono or di-halo $C_{1-4}$ alkyl including dichloromethane; etheral solvents such as diethyl ether di-n-butyl and diisopropyl ethers, cyclic ethers such as tetrahydropyran, and tetrahydrofuran; aromatic solvents such as benzene, toluene and xylene; and $C_{6-10}$ linear, branched or cyclic hydrocarbon solvent including hexane.

For purposes of this specification non-reactive solvents include halocarbon solvents such as mono or di-halo $C_{1-4}$ alkyl including dichloromethane.

Optionally, a standard phase transfer agent such as tetra-n-butylammonium salts and polyethylglycol reagents such as TWEEN 40 may be added to the reaction mix (0 to 5% of total volume).

The molar ratio of compound B to

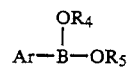

should be approximately 1 to 1 or greater; preferably 1.2 to 1, The molar ratio of palladium catalyst to compound B should be approximately 0.01 or greater; preferably 0.06 to 0.10, The reaction is allowed to proceed until substantially complete in 1-24 hours (solvent dependent).

For purposes of this specification transition metal catalyst is defined to include Pd° catalysts including Pd (dba)$_2$, Pd$_2$ (dba) 3, Pd$_2$ (dba)$_3$.CHCl$_3$ wherein dba is defined as dibenzyledineacetone. As appreciated by those of skill in the art, other standard coordinating ligands may also be used. Pd$^{II}$ catalysts may also be employed including Pd(OAc)$_2$ and PdCl$_2$. Nickel catalysts may also be used.

The compound of Formula 1 can then be converted to active antibiotic by methods known in the art, as exemplified in U.S. Pat. Nos. 5,034,384 and 5,011,832 which are hereby incorporated by reference.

In a second embodiment the invention concerns intermediate compounds of formula

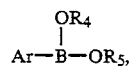

as defined above.

SCHEME 1

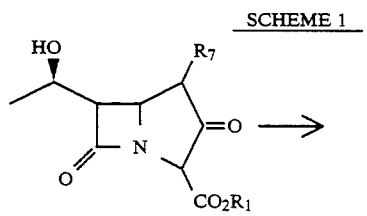

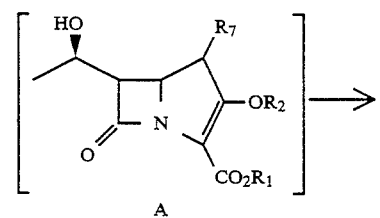
A

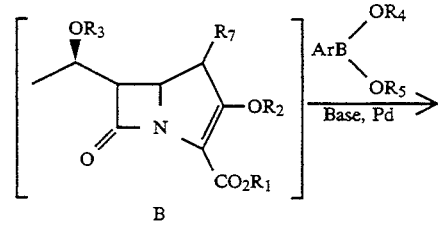
B

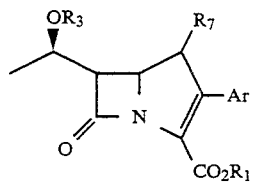

SCHEME 2

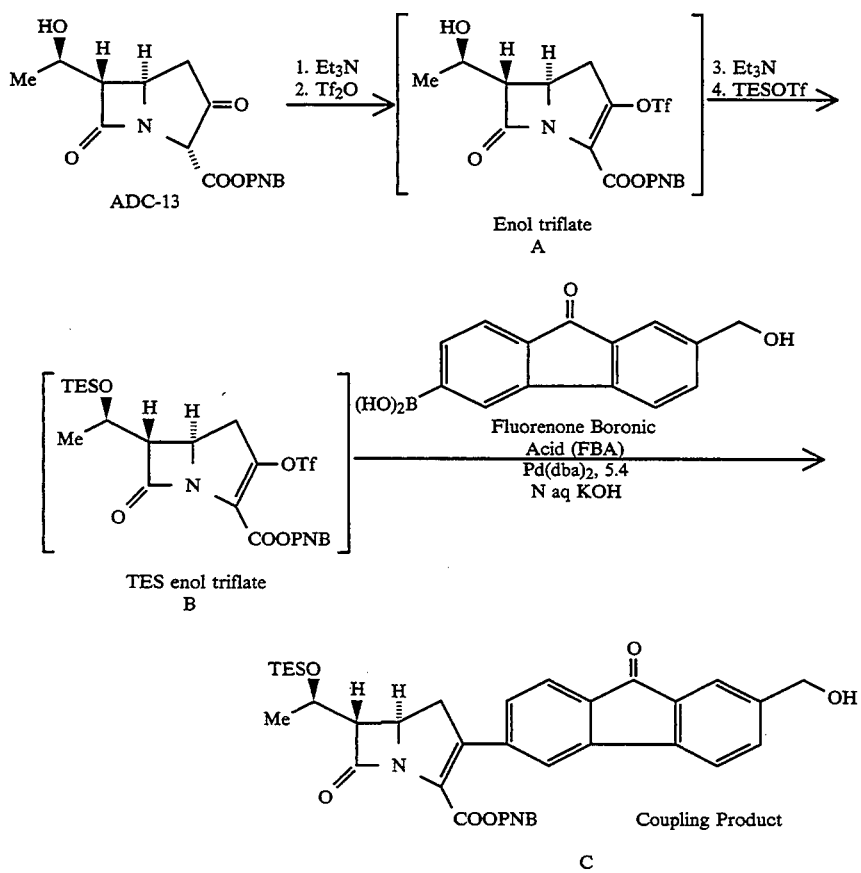

hereby incorporated by reference. Please also note that in the following Examples the compound of Formula 2 is identified as ADC-13.

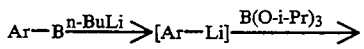

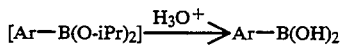

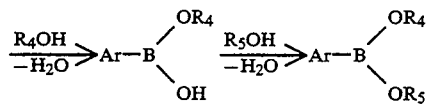

Preferred definitions of Ar include those wherein $R^b$ and $R^c$ are each —CH$_2$OH, —OCH$_3$, —CH$_3$ or triethylsilyloxymethyl. $R^b$ preferably resides a position 6 or 7 of the fluorenone and $R^c$ is preferably at position 4 of the biphenyl.

The method of preparation is shown in Scheme 2 and further detailed in the Examples. In overview, the bromide, Ar-Br undergoes metallation with n-butyl lithium; is then boronated with B(O-i-propyl)$_3$; and is then acidified to form Ar-B(OH)$_2$. Further reaction with R$_4$OH and R$_5$OH (R$_4$ and R$_5$ defined on page 11) provides the intermediate boronic esters.

As Exemplified hereinunder, the group Ar may optionally contain a carbonyl or other group that required protection prior to further processing.

The following examples illustrate the preparation of representative compounds of the invention and as such are not considered as limiting the invention as set forth in the claims. For further methods of preparing substituted fluorenonyl and biphenyl compounds please see U.S. Pat. Nos. 5,034,384 and 5,011,832 which are Preparation of p-Nitrobenzyl (5R,6S)-2[7-hydroxymethyl-9-fluorenone-3yl]-6-(1R-triethylsilyloxymethyl)-carba-pen-2-em -3-carboxylate dimethylformamide mono-solvate Anhydrous dichloromethane (7.6 L, 11.5 mL/g of ADC-13 KF≦50 mg/mL) was charged to a dry flask under an N$_2$ atmosphere. ADC-13 (660 g, 1.88 mol) was added as a solid and the solution was cooled to —78° C. (thick slurry). Triethylamine (249.5 mL, 181 g, 1.79 mol) was added over approximately 30 minutes. After 15–25 minutes, trifluoromethanesulfonic anhydride (302.4 mL, 505 g, 1.79 mol) was added over 75 minutes. Triethylamine (275.7 mL, 200 g, 1.98 mol) was added over approximately 25–30 minutes, maintaining the internal temperature below —70° C. After 15–25 minutes, triethylsilyl trifluoromethanesulfonate (447.3 mL, 523 g, 1.98 mol) was added over 70–75 minutes, maintaining the internal temperature below —70° C. The mixture was aged at —70° to 80° C. for 45–65 minutes.

A separate dry flask was charged with anhydrous dimethylformamide (3.6 L, 9.0 mL/g boronic acid) and the hydroxymethylfluorenylboronic acid (400 g, 1.57 mol) at ambient temperature under N$_2$ atmosphere. This solution was added to the TES enol triflate solution (internal temperature maintained ≦—60° C.) over 35 minutes. To the resulting mixture was added bis(dibenzylideneacetone)palladium (0) (54.4 g, 94.2 mmol, 0.06 mol/mol boronic acid) as a solid and 5.67N aqueous KOH (830.7 mL, 4.71 mol, 3.0 mol/mol boronic acid). The mixture was allowed to warm to ambient temperature and stir for four hours. Ethyl acetate (3 L) was added and the dichloromethane was removed by vacuum concentration to a volume of 6.3 L. The resulting dark mixture was diluted with EtOAc (15 L), and H$_2$O (10 L). The dark layers were separated and the aqueous layer was back extracted with EtOAc (10 L). The combined organic layers were quantitatively assayed by HPLC and then dried by azeotropic distillation of water and concentrated to 4.0 L.

The ethyl acetate solution was turned over to acetonitrile by distillation. The blackish-red mixture was concentrated to a final volume of 17.3 L. Water (3.48 L; 20 v/v % of the acetonitrile mixture) was added. The resulting mixture was agitated for 30 minutes. Black free flowing solids formed. The solids were removed by filtration and washed (1.44 L of 17% water in acetonitrile). The clear reddish yellow filtrate (HPLC assay showed 720 g product) was then loaded on to an SP-206 resin column (18 L of resin) at a flow rate of 2 b.v/h (0.5 b.v fractions [9 L]). The column was eluted with: 3 b.v. (54 L) of 70/30 acetonitrile/water, 2 b.v. (36 L) of acetonitrile, and 7 b.v. (126 L) of 50/50 2-butanone/acetonitrile.

The appropriate fractions (assayed to contain 720 g product) were combined and turned over to dimethylformamide (DMF) by distillation (final volume=32 L, 45 mL/g assayed product). Water (8.6 L, 12 mL/g assayed product) was added over 5 minutes. The temperature rose from 30° to 36° C. The solution was cooled to 30° C. and was seeded (5% by weight). Crystallization occurred and a yellow slurry formed as the mixture was aged at 30° C. for 0.5 hours. More water (8.6 L) was added over 4 hours (final DMF:water=15:8). The slurry was cooled to 0.5° C. over 45 minutes and aged for 1 hour. The crystals were collected by filtration and washed with cold DMF:water (15:8; 5° C.; 7.2 L,) and water (ambient temperature; 2×7.2 L). The wet cake was dried in vacuo (N$_2$ sweep, over P$_2$O$_5$) to give 720 g (63% yield) of the coupled product as its DMF solvate (98 area % purity).

EXAMPLE 2

Preparation of p-Nitrobenzyl (5R,6S)-2-phenyl-6-(1R-triethylsilyloxy-methyl)-carba-pen-2-em-3-carboxylate

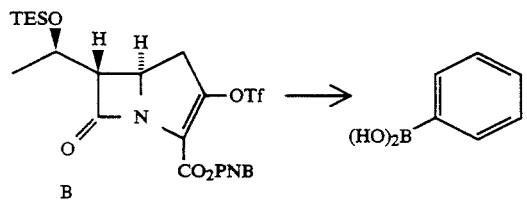

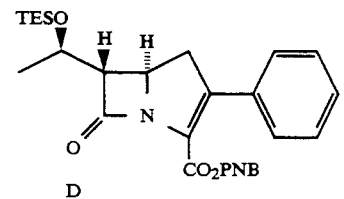

A solution of p-nitrobenzyl 7-[(1R)-1-triethylsilyloxyethyl]-2-trifluoromethane-sulfonyloxy-3-carbapenem 4-carboxylate (1 mmol), prepared as in Example 1, was diluted with toluene (4.7 mL) at −78° C. To the solution was added phenylboric acid (159 mg, 1.3 mmol.), potassium carbonate (359 mg, 2.6 mmol), TWEEN 40 (2drops), and Pd$_2$(dba)$_3$CHCl$_3$ (20.3 mg) and the mixture was stirred for 4 hours at ambient temperature. The mixture was diluted with ethyl acetate, washed with saturated aqueous ammonium chloride and saturated aqueous sodium chloride, dried over magnesium sulfate, and purified by silica gel chromatography using ethyl acetate and n-hexane=1.5:8.5 to give 319 mg of p-nitrobenzyl 2-phenyl-7-{[(1R)-1-triethyl-silyloxyethyl]-3-carbapem-4-carboxylate (61.0%) as a crystalline solid.

$^1$HNMR (250 MHz CDCl$_3$) δ0.63 (6H, m), 0.97 (9H, t, J=7.8 Hz), 1.32 (3H,d,J=6.2 Hz), 3.14–3.31 (3H, m), 4.22–4.35 (2H, m), 5.20 and 5.36 (2H, ABq, J=13.9 Hz), 7.35 (5H, s), 7.44 and 8.16 (4H, ABq, J=8.6 Hz). $^{13}$C NMR (62.5 MHz, CDCl$_3$) δ4.94, 6.80, 22.72, 42.65, 52.50, 65.31, 66.17, 67.34, 123.61, 126.65, 127.99, 128.06, 128.18, 129.04, 133.27, 142.69, 145.85, 147.54, 160.56, and 176.51. IR (neat) 2960, 2880, 1765, 1720, 1605, 1515, 1345, 1270, and 1190 cm$^{-1}$.

EXAMPLE 3

Preparation of p-Nitrobenzyl (5R,6S)-2-[7-methoxymethyl-9-fluorenone-3-yl]-6-(1R-triethyl-silyloxymethyl)-carbapen-2-em-3-carboxylate.

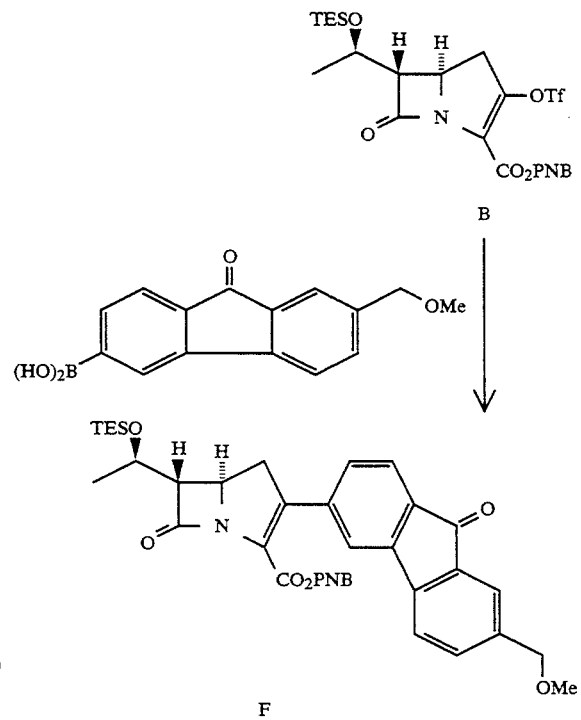

To a solution of ADC-13 (348 mg, 1 mmol) in anhydrous tetrahydrofuran (THF) (4 mL) was added diisopropylamine (0.154 mL, 1.1 mmol) at −70° C. After 15 minutes stirring at −70° C., tifluoromethanesulfonic anhydride (0.185 mL, 1.1 mmol) was added at 72° C. to −64° C., and the mixture was stirred at −78° C. for 20 minutes. To this mixture was added triethylamine (0.153 mL, 1.1 mmol) followed by triethylsilyl trifluoromethanesulfonate (0.249 mL, 1.1 mmol) at −78° C. and the mixture stirred for 30 minutes at −78° C. To the reaction mixture was added 2-methoxymethylfluorene-9-one-6-boric acid (201 mg, 0.75 mmol), potassium carbonate (207 mg, 1.5 mmol). Pd$_2$(dba)$_3$CHCl$_3$ (20 mg, 0.0196 mmol), and TWEEN 40 (3 drops) at −78° C. and the mixture was allowed to warm to ambient temperature. After stirring for 1.5 hours, additional potassium carbonate (20 mg) and Pd₂(dba)₃CHCl₃ (5 mg) was added. The mixture was stirred for additional 4 hours at ambient temperature. The reaction mixture was diluted with ethyl acetate (20 mL) and washed with water (20 mL). The aqueous layer was separated and extracted with ethyl acetate (10 mL). The extract and washings were combined, dried over magnesium sulfate, and purified by silica gel chromatography using ethyl acetate and n-hexane (1:4) (v/v) to give p-nitrobenzyl 2-(2-methoxymethylfluorene-9-one-6-yl)-7-{(1R)-1-triethylsilyloxy-ethyl]-3-carbapem-4-carboxylate (219 mg, 43.7%) as an amorphous solid.

¹H NMR (CDCl₃, 250 MHz) δ7.96 (d, J=8.7 Hz, 2H), 7.52–7.23 (overlapping m, 7H), 7.13 (dd, J=7.6, 1.0 Hz, 1H), 5.26 (d, J=13.6 Hz, 1H), 5.09 (d, J=13.6 Hz, 1H), 4.36 (s, 2H), 4.40–4.15 (m, 2H), 3.32 (s, 3H), 3.40–3.22 (m, 3H), 1.22 (d, J=6.1 Hz, 3H), 0.88 (t, J=7.9 Hz, 9H), 0.58–0.49 (m, 6H) ¹³C NMR (CDCl₃) δ192.54, 176.11, 160.13, 147.33 143.96, 143.84, 142.84, 142.13, 140.08, 139.74, 134.28, 134.05, 133.60, 128.28, 128.18, 127.99, 123.77, 123.38, 120.14, 119.96, 73.72, 67.34, 65.70, 65.44, 58.27, 52.27 42.22, 22.47, 6.65, 4.75. IR (Nujol) 1770, 1710, 1515, 1345, 1265, 1190, 1100 cm⁻¹.

EXAMPLE 4

Preparation of p-Nitrobenzyl (5R,6S)-2-[7-methyl-9-fluorenon-3-yl]-6-(1R-triethylsilyloxy-methyl)-carbapem-2-em-3-carboxylate.

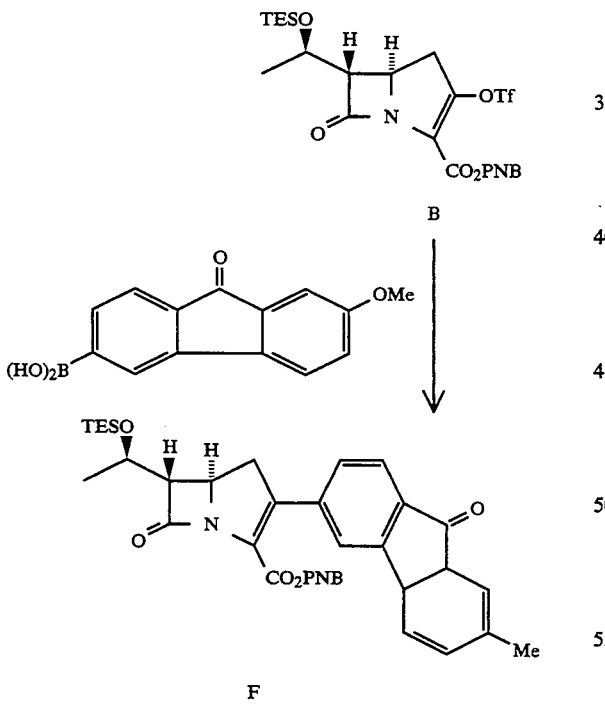

Anhydrous THF (10 mL) was charged to a dry flask under N₂. ADC-13 (496 mg, 1.43 mmol) was added and the solution was cooled to −78° C. Di-iso-propylamine (221μL, 159 mg, 1.58 mmol) was added slowly, giving an orange solution. After 15 minutes, trifluoromethanesulfonic anhydride (266 μL, 446 mg, 1.58 mmol) was added dropwise (T≦−73° C.), giving the intermediate ADC-13 enol triflate. After 1 hour, triethylamine (219 μL, 159 mg, 1.58 mmol) was added dropwise, followed by triethylsilyl trifluoromethanesulfonate (357 μL, 417 mg, 1.58 mmol) (T≦−71° C.). The pale yellow mixture was aged for 1 hour. More triethylamine (100 μL) and triethylsilyl trifluoromethanesulfonate (160 μL) were added to consume any remaining ADC-13 enol triflate. After 15 minutes, a solution of TWEEN 40 (14 mg) in toluene (10 mL) was added, followed by a suspension of the methylfluorenylboronic acid (323 mg, 1.36 mmol) in 1M aqueous K₂CO₃ (11.4 mL, 11.4 mmol). This mixture was warmed to ambient temperature, degassed with a stream of N₂, and tris(dibenzylidene-acetone)dipalladium chloroform complex (30 mg, 0.0286 mmol) was added. This mixture was stirred at ambient temperature for 29 hours. This mixture was diluted with i-PrOAc (30 mL) and was washed with H₂O (1×25 mL) and 1N aqueous Na₂CO₃ (1×25 mL). The combined aqueous washings were extracted with i-PrOAc (1×10 mL). The combined organic extracts were washed with saturated aqueous NH₄Cl (1×25 mL) and brine (1×25 mL). The organic layer was dried over anhydrous MgSO₄, filtered, and purified by flash chromatography over silica gel (20% EtOAc in hexanes, then 30% EtOAc in hexanes as eluant) to give 360 mg (50% yield) of the title compound as a glassy yellow oil (purity ca. 90% by ¹H NMR analysis):

¹H NMR (250 MHz, CDCl₃) δ8.18 (m, 2H), 7.60 (m, 1H), 7.48 (m, 3H), 7.38 (m, 1H), 7.25 (m 3H), 5.28 (ABq, J$_{AB}$=13.5 Hz, Δv$_{AB}$=41.4 Hz, 2H), 4.31 (m, 2H), 3.30 (m, 3H), 2.39 (s, 3H) 1.32 (d, J=6.2 Hz, 3H), 0.98 (t, J=8.1 Hz, 9H) 0.64 (m, 6H).

EXAMPLE 5

Preparation of p-Nitrobenzyl (5R, 6S)-2-[7-triethylsilyloxymethyl-9-fluorenon-3-yl]-6-(1R-triethylsilyloxy-methyl)-carbapen-2-em-3-carboxylate

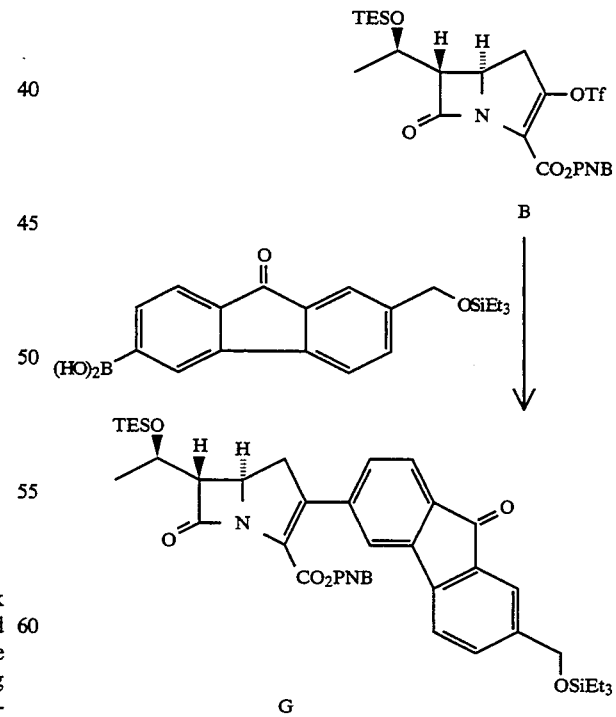

A solution of ADC-13 (0.273 g, 0.78 mmol) in the THF (3 mL) was treated with di-iso-propylamine (0.122 mL, 1.1 eq) at −78° C. After 15 minutes, trifluoromethanesulfonic acid anhydride (0.145 mL, 1.1 eq) was added and the mixture stirred at −78° C. for 20 min. Triethylamine (0.122 mL, 1.1 eq) was added followed by triethylsilyl trifluoromethanesulfonate (0.196 mL, 1.1 eq). The mixture was stirred at −78° C. for 1 hour. To this mixture was added triethylsilyloxymethyl-fluorenylboronic acid (0.1 g, 0.35 eq) in a solution of toluene: tetrahydrofuran (4:1). Catalyst (Pd2(dba)3CHCl3 (0.021 g)) and aqueous KOH (5.4N, 0.55 mL, 3.0 eq) were added and the mixture stirred at ambient temperature for 16 hours. The mixture was diluted with ethyl acetate (30 mL) and washed with water (30 mL). The organic phase was dried over anhydrous MgSO4 and purified by silica gel chromatography (ethyl acetate:hexane) to give 190 mg (91% yield of the title compound as an amorphous solid.

$^1$HNMR (250 mHZ, CDCl3) d 0.53 (m, 12H), 1.0 (m, 18H), 1.25 (d, 3H), 3.3 (m, 3H), 4.2–4.4 (m, 2H), 4.7 (s, 2H) 5.15 and 5.4 (2H) 7.1–7.7 (m, 8H), 8.1 (d, 2H).

EXAMPLE 6

Preparation of p-Nitrobenzyl (5R,6S)-2-[3-cyano-5-(4-hydroxymethylphenyl)-phenyl]-6-[(1R)-triethyl-silyloxyeth-1-yl]carbapen-2-em-3-carboxylate.

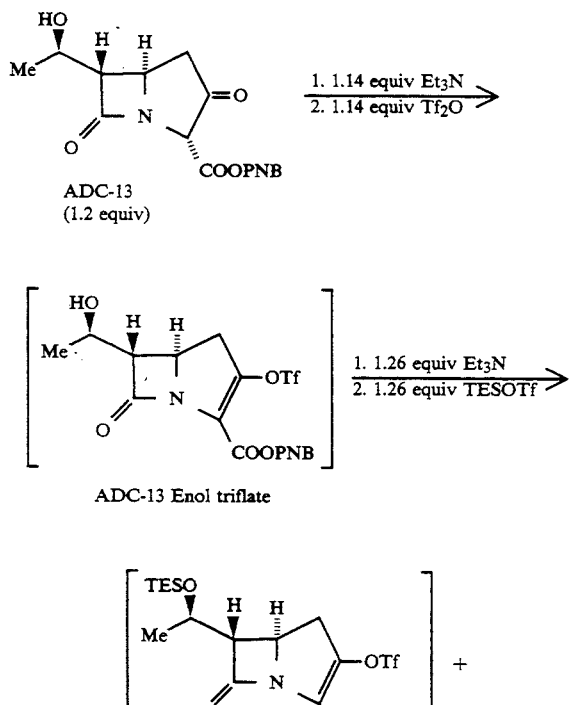

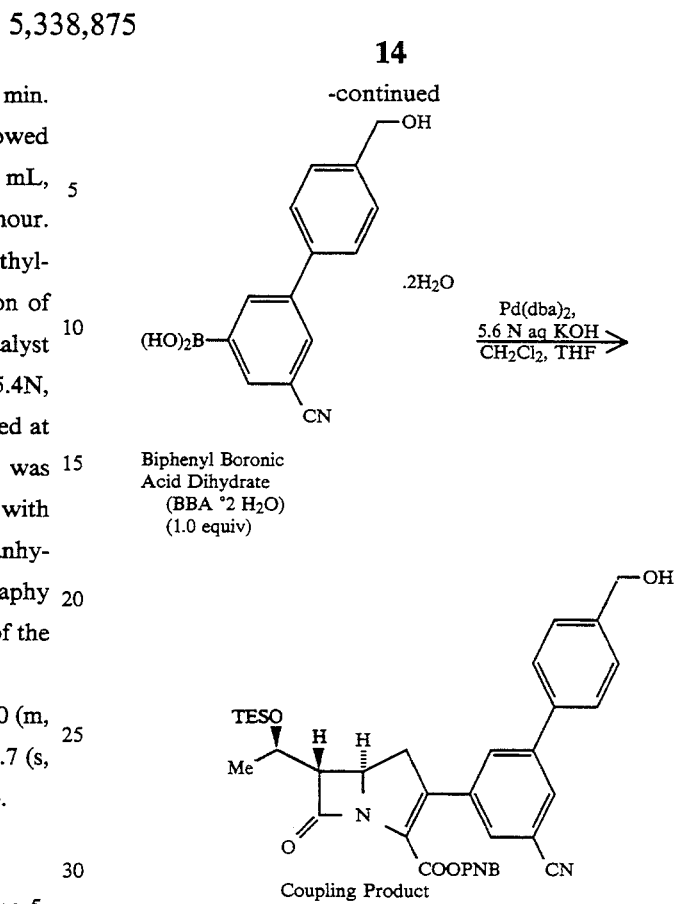

Dry dichloromethane (330 mL, 11.5 mL/g ADC-13, KF≦100 mg/mL) was charged to a dry flask under a dry N2 atmosphere. ADC-13 (28.9 g, 83.0 mmol) was added as a solid and the solution was cooled to −78° C. Triethylamine (11.0 mL, 7.9 g, 78.8 mmol, KF≦100 mg/mL) was added over approximately 5 min, maintaining the internal temperature below −70° C. After 15 min, trifluoromethanesulfonic anhydride (13.3 mL, 22.2 g, 78.8 mmol) was added over approximately 15 min (exothermic!), maintaining the internal temperature below −70° C. After 15 min, triethylamine (12.1 mL, 8.8 g, 87.2 mmol, KF≦100 mg/mL) was added over approximately 5 min, maintaining the internal temperature below −70° C. After 15 min, triethylsilyl trifluoromethanesulfonate (19.7 mL, 23.0 g, 87.2 mmol) was added over approximately 15 min (exothermic!), maintaining the internal temperature below −70° C. The mixture was aged at −70° to −80° C. for 30 min.

In a separate flask, the BBA•2H2O (20.0 g, 69.2 mmol) was dissolved in THF (630 mL) and the solution was added to the enol triflate solution by cannula, maintaining the internal temperature below −60° C. Bis(-dibenzylideneacetone)palladium(0) (1.2 g, 2.08 mmol) was added, followed by 5.6N aq KOH (37 mL, 208 mmol), maintaining the internal temperature below −60° C. The cold bath was removed and the dark mixture was allowed to warm to ambient temperature.

The reaction was quenched by pouring the mixture into 0.2M aq KH2PO4 (not pH adjusted, 1.1 L), EtOAc (1.3 L), and MeOH (220 mL). The mixture was agitated and the phases (both slightly cloudy) were separated. The aqueous layer was extracted with EtOAc (1×650 mL). The combined organic extracts were concentrated in vacuo and the residue (dark oil) was flushed with acetonitrile (2×165 mL). The blackish-red residue was diluted to a final volume of 720 mL (the mixture was very turbid and dark brown in color; insoluble palladium compounds are present).

Water (145 mL; 20 v/v % of the acetonitrile mixture) was added over 1 min. The resulting mixture was agitated for 30 min. Black free-flowing solids formed. The solids were removed by filtration and washed (60 mL of 17% water in acetonitrile). The clear reddish yellow filtrate (900 mL; approximate solvent composition is 16% water in acetonitrile; 1 bed-volume; an HPLC assay was run to determine concentration of the column feed) was then loaded onto an SP-206 resin column (900 mL of resin).

Column Preparation

SP-206 resin (Mitsubishi; 900 mL resin; 45 mL resin/g of biphenylboronic acid) was swelled in 50% aqueous methanol. The resin was loaded onto a column. The resin was washed with 2 b.v. (1800 mL) of acetone, 2 b.v. (1800 mL) of acetonitrile (ACN), and 2 b.v. (1800 mL) 70/30 ACN/water.

Chromatography

The column feed (1 b.v., 900 mL, assayed to contain ca. 39 g of product, ca. 85% yield from BBA•2H$_2$O) was loaded onto the resin (ambient temperature) at a flow rate of 3–5 b.v./h (0.5 b.v. fractions [450 mL]). The column was eluted with: 3 b.v. (2700 mL) 70/30 acetonitrile/water, followed by 3.5 b.v. (3150 mL) acetonitrile.

The appropriate fractions (minimum collected fraction purity was 91 area %; combined fraction purity was 95 area %; assayed to contain 31.2 g product) were combined and evaporated in vacuo to give a pale yellow, oily foam (34.55 g, 72% from BBA•2H$_2$O, 95 wt % pure vs. working std, 95 area % pure (270 nm)).

The following additional compounds were prepared by the analogous procedure:

1. Preparation of p-Nitrobenzyl-(5R,6S)-2-(4'-t-butyldiphenylsiloxymethylphenyl)-6-[(1R-triethylsilyloxyeth-1-yl)]-carbapen-2-em-3-carboxylate

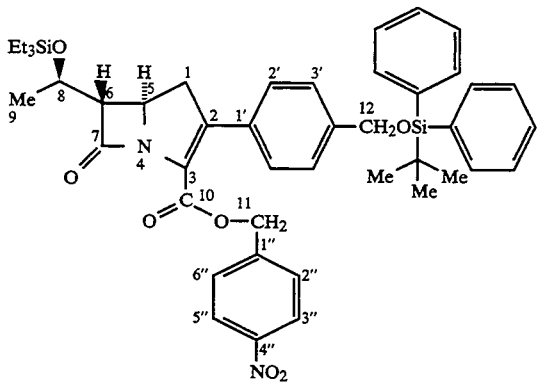

$^1$H NMR (CDCl$_3$, 250 MHz) δ8.18 (overlapping m, 2H), 7.75 (m, 4H), 7.35–7.58 (m, 12H), 5.43 (d, J=14.0 Hz, 1H), 5.25 (d, J=14.0, 1H), 4.84 (s, 2H), 4.27–4.47 (overlapping m, 2H), 3.40 (dd, J=18.1, 8.9 Hz, 1H), 3.32 (overlapping m, 1H), 3.26 (dd, J=18.1, 10.0 Hz, 1H), 1.38 (d, J=6.3 Hz, 3H), 1.17 (s, tBu, 9H), 1.03 (t, J=7.6 Hz, Me, 9H), 0.07 (m, 6H). $^{13}$C NMR (CDCl$_3$) δ176.29, 160.46, 147.29, 145.72, 142.62, 142.06, 135.31, 133.02, 131.47, 129.59, 127.88, 127.58, 126.08, 125.29, 123.48, 123.33, 67.02 and 65.82, 65.05 and 64.91, 52.08, 42.27, 26.63, 22.47, 19.10, 6.62, 4.75. IR (neat) 2973, 2895, 1769, 1720, 1608, 1522, 1347, 702 cm$^{-1}$.

2. Preparation of p-Nitrobenzyl-(5R,6S)-2-(3'-nitrophenyl)-6-[(1R-triethylsilyloxyeth-1-yl)]-carbapen-2-em-3-carboxylate

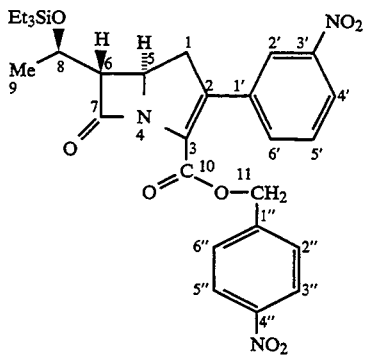

$^1$H NMR (CDCl$_3$, 250 MHz) δ8.24 (t, J=1.9 Hz, 1H), 8.12–8.23 (overlapping m, 3H), 7.72 (m, 1H), 7.56 (m, 2H), 7.52 (t, J=8.5 Hz, 1H), 5.38 (d, J=14.0 Hz, 1H), 5.22 (d, J=14.0 Hz, 1H), 4.38 (ddd, J=10.2, 8.8, 3.0 Hz, 1H), 4.23–4.34 (m, 1H), 3.40 (dd, J=18.6, 8.8 Hz, 1H), 3.32 (dd, J=5.6, 3.0 Hz, 1H), 3.24 (dd, J=18.6, 10.2 Hz, 1H), 1.32 (d, J=6.0 Hz, 3H), 0.96 (t, J=7.8 Hz, 9H), 0.62 (m, 6H). $^{13}$C NMR (CDCl$_3$) δ176.14, 160.18, 147.91, 147.68, 142.38, 142.32, 134.77, 134.14, 129.13, 128.45, 128.29, 123.70, 123.59, 123.18, 67.63, 65.77, 65.70, 52.22, 42.22, 22.64, 6.79, 4.92. IR (neat) 2980, 2895, 1790, 1727, 1525, 1350, 1275, 1200, 750 cm$^{-1}$.

3. Preparation of p-Nitrobenzyl-(5R,6S)-2-(2'-thiopheno)-6-[(1R-triethylsilyloxyeth-1-yl)]-carbapen-2-em-3-carboxylate

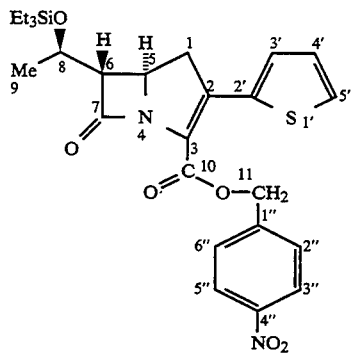

$^1$H NMR (CDCl$_3$, 250 MHz) δ8.20 (dd, J=8.7, 2.2 Hz, 2H), 7.67 (d, J=8.6 Hz, 2H), 7.58 (dd, J=3.8, 1.0 Hz, 1H), 7.48 (dd, J=5.1, 1.0 Hz, 1H), 7.06 (dd, J=5.1, 3.8 Hz, 1H), 5.50 (d, J=14.0 Hz, 1H), 5.28 (d, J=14.0 Hz, 1H), 4.28–4.18 (m, 2H), 3.45 (dd, J=17.6, 9.8 Hz, 1H), 3.35 (dd, J=17.6, 9.3 Hz, 1H ), 3.18 (dd, J=−5.9, 2.8 Hz, 1H), 1.29 (d, J=7.8 Hz, 3H), 0.94 (t, J=7.8 Hz, 9H), 0.64–0.55 (m, 6H). $^{13}$C NMR (CDCl$_3$) δ176.13, 161.09, 147.58, 143.01, 138.56, 134.32, 131.62, 130.33, 128.12, 127.16, 123.68, 123.49, 67.09, 65.89, 65.38, 51.47, 42.04, 22.70, 6.78, 4.91. IR (Nujol) 1770, 1705, 1600, 1565, 1515, 1340, 1325, 1280, 1255, 1195 cm$^{-1}$.

4. Preparation of

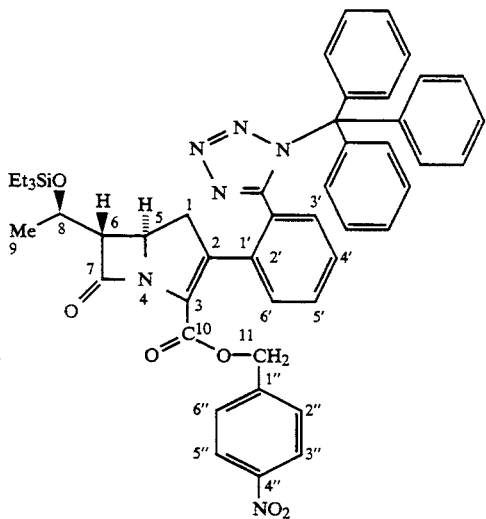

¹H NMR (CDCl₃, 250 MHz) δ8.12 (m, 1H), 7.99 (m, 2H), 7.34–7.27 (m, 9H), 7.18 (m, 1H), 7.13–7.04 (m, 8H), 5.01 (d, J=13.8 Hz, 1H), 4.86 (d, J=13.8 Hz, 1H), 4.14 (q, J=5.9 Hz, 1H), 3.78 (broad, 1H), 2.99 (broad, 2H), 2.89 (dd, J=18.4, 9.9 Hz, 1H), 1.16 (d, J=6.2 Hz, 3H), 0.91 (t, J=7.9 Hz, 9H), 0.60–0.50 (m, 6H).

5. Preparation of p-Nitrobenzyl-(5R,6S)-2-(3'-cyanophenyl)-6-[(1R-triethylsilyloxyeth-1-yl)]-carbapen-2-em-3-carboxylate

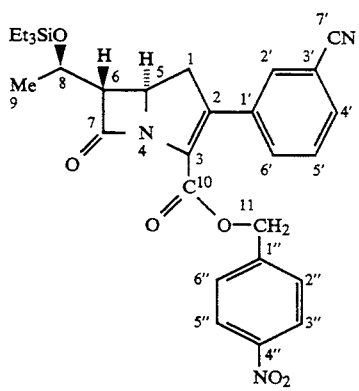

¹H NMR (CDCl₃, 250 MHz) δ8.16 (m, 2H), 7.65–7.40 (m, 6H), 5.36 (d, J=13.8 Hz, 1H), 5.19 (d, J=13.8 Hz, 1H), 4.40–4.23 (m, 2H), 3.43–3.26 (m, 2H), 3.18 (dd, J=18.3, 10.1 Hz, 1H), 1.29 (d, J=6.1 Hz, 3H), 0.95 (t, J=7.8 Hz, 9H), 0.65–0.56 (m, 6H).

¹³C NMR (CDCl₃, 62.9 Hz) δ176.20, 160.18, 147.64, 142.61, 142.41, 134,53, 132.43, 132.15, 131.70, 129.02, 128.25, 128.16, 123.68, 118.27, 112.45, 67.54, 65.76, 65.61, 52.20, 42.19, 22.61, 6.79, 4.91.

6. Preparation of p-Nitrobenzyl-(5R,6S)-2-(4'-trifluoromethylphenyl)-6-[(1R-triethylsilyloxyeth-1-yl)]-carbapen-2-em-3-carboxylate

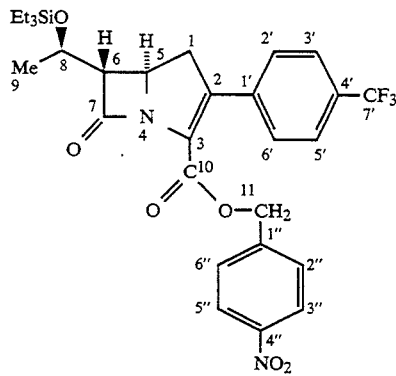

¹H NMR (CDCl₃, 250 MHz) δ8.13 (m, 2H), 7.60–7.43 (m, 6H), 5.35 (d, J=13.8 Hz, 1H), 5.18 (d, J=13.8 Hz, 1H), 4.42–4.22 (m, 2H), 3.43–3.27 (m, 2H), 3.20 (dd, J=18.4, 10.1 Hz, 1H), 1.30 (d, J=6.1 Hz, 3H), 0.96 (t, J=7.8 Hz, 9H), 0.68–0.55 (m, 6H).

7. Preparation of p-Nitrobenzyl-(5R,6S)-2-styryl-6-[(1R-triethylsilyloxyeth-1-yl)]-carbapen-2-em-3-carboxylate

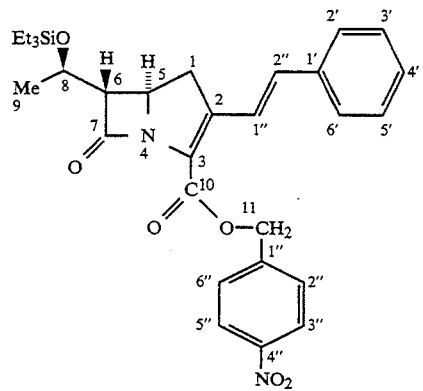

¹H NMR (CDCl₃, 400 MHz) δ8.24 (m, 2H), 7.92 (d, J=16.3 Hz, 1H), 7.71 (m, 2H), 7.48 (m, 2H), 7.37–7.27 (m, 3H), 6.72 (d, J=16.3 Hz, 1H), 5.51 (d, J=13.9 Hz, 1H), 5.31 (d, J=13.9 Hz, 1H), 4.32–4.21 (m, 2H), 3.25 (dd, J=17.6, 10.4 Hz, 1H), 3.20 (dd, J=6.2, 3.0 Hz, 1H), 3.13 (dd, J=17.6, 8.7 Hz, 1H), 1.32 (d, J=6.1 Hz, 3H), 0.98 (t, J=7.9 Hz, 9H), 0.67–0.61 (m, 6H). ¹³C NMR (CDCl₃, 100 Mz) δ175.93, 160.94, 147.62, 144.85, 143.07, 136.78, 136.27, 129.00, 128.80, 128.09, 127.23, 126.73, 123.74, 121.34, 67.12, 66.09, 65.23, 52.60, 36.75, 22.68, 6.80, 4.95. IR (Nujol) 1755, 1710, 1610, 1575, 1565, 1520, 1345, 1290, 1280, 1270, 1230, 1200, 1155, 1110, 1070, 1015 cm⁻¹.

8. Preparation of p-Nitrobenzyl-(5R,6S)-2-(2'-methoxyphenyl)-6-[(1R-triethylsilyloxyeth-1-yl)]carbapen-2-em-3-carboxylate

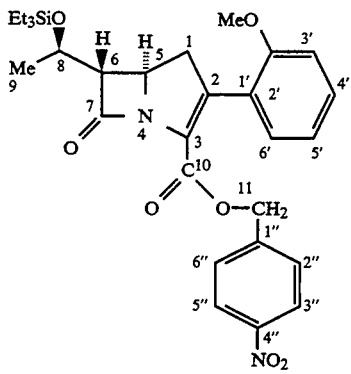

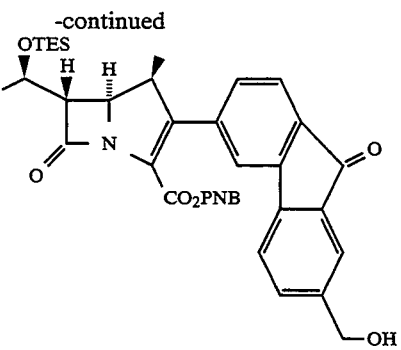

¹H NMR (CDCl₃, 250 MHz)δ8.08 (m, 2H), 7.34–7.23 (m, 3H), 7.13 (dd, J=7.5, 1.7 Hz, 1H), 6.94–6.83 (m, 2H), 5.27 (d, J=14.1 Hz, 1H), 5.12 (d, J=14.1 Hz, 1H), 4.35–4.19 (m, 2H), 3.73 (s, 3H), 3.31 (dd, J=18.3, 8.8 Hz, 1H), 3.24 (dd, J=6.5, 2.9 Hz, 1H), 3.09 (dd, J=18.3, 10.0 Hz, 1H), 1.30 (d, J=6.2 Hz, 3H), 0.95 (t, J=7.9 Hz, 9H), 0.68–0.52 (m, 6H). ¹³C NMR (CDCl₃, 62.9 MHz) δ176.70, 160.49, 156.26, 147.41, 143.42, 142.88, 129.98, 129.46, 128.16, 127.81, 123.51, 122.95, 120.34, 110.83, 67.24, 66.34, 65.04, 55.37, 53.19, 41.80, 22.72, 6.81, 4.95. IR 2970, 2890, 1770, 1720, 1610, 1600, 1520, 1480, 1460, 1440, 1380, 1350, 1270, 1195 cm⁻¹.

EXAMPLE 7

Preparation of p-Nitrobenzyl (1S,5R,6S)-1-methyl-2-(7-hydroxymethyl-9-fluorenone-3-yl)-6-(1R-triethylsilyloxyethyl)-carbapen-2-em-3-carboxylate.

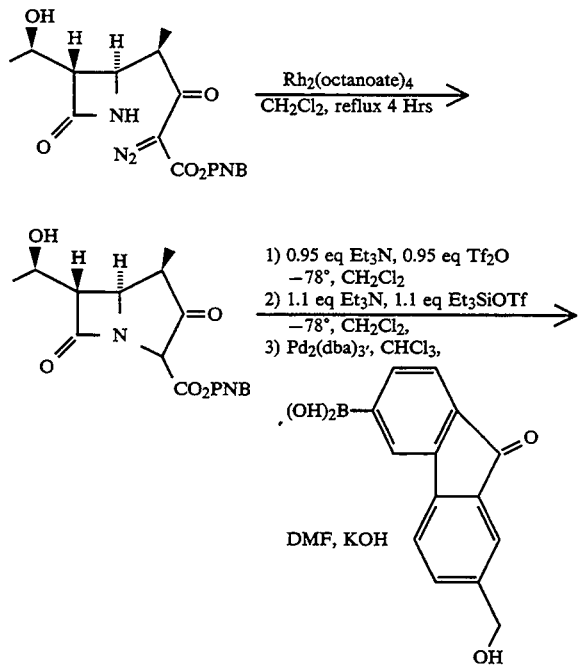

p-Nitrobenzyl (1R,5R,6S) 1-methyl 2-oxo 6-(1R-hydroxyethyl)-carbapenam-3-carboxylate (3S,4R)-3-[(1R)-1-hydroxyethyl]-4-[(1R)-1-methyl-3-diazo 3-p-nitrobenzyloxycarbonyl-2-oxopropyl]-azetidin-2-one (390 mg, 1 mmol) was dissolved in anhydrous methylene chloride (8 ml) and treated with Rhodium octanoate (3 mg). The reaction mixture was refluxed under nitrogen for 4 hours then allowed to cool and evaporated under reduced pressure to give the desired cyclized product which was used for the next reaction without further purification.

p-Nitrobenzyl (1S,5R,6S)-1-methyl-2-(7-hydroxymethyl-9-fluorenone-3-yl)-6-(1R-triethylsilyloxyethyl)-carbapen-2-em-3-carboxylate The product from the previous reaction was dissolved in methylene chloride (4 ml) and cooled to −78°, under nitrogen. Triethylamine (133 μl, 0.95 eq.) was added dropwise and the reaction mixture was stirred for 15 minutes followed by dropwise addition of trifluoromethanesulfonic anhydride (159 μl, 0.95 eq.). The reaction mixture was stirred at −78° for 25 min. To this was added triethylamine (153 μl, 1.1 eq) dropwise followed 15 minutes later, by triethylsilyl trifluoromethanesulfonate (193 μl, 1.1 eq) also added dropwise. The reaction mixture was stirred another 1.25 hours at the end of which TLC showed complete reaction to the triethylsilyl derivative. The hydroxymethylflourenone-boronic acid (254 mg, 1.0 eq) was dissolved in DMF (2.2 ml) and added dropwise to the reaction mixture followed by Pd₂(dibenzylideneacetone)₃CHCl₃ (21 mg) and KOH solution (0.52 ml, 5.67N). The reaction mixture was stirred at −78° for 10 minutes and then allowed to warm to room temperature in 15 minutes and then stirred at 30° for 3.5 hours. TLC showed complete reaction of the enoltriflate.

The reaction mixture was diluted with 20% EtOAc/Et₂O (50 ml) and washed four times with water (25 ml) and then with brine. The organic phase was dried over Na₂SO₄ and evaporated to give a residue (502 mg). Chromatography on silica gel plates (35% EtOAc/hexane eluant) gave the product (331 mg).

NMR (200 MHz, CDCl₃): δ0.62 (q, J=7, CH₃—CH₂Si); 0.97 (t, J=7, CH₃—CH₂—Si); 1.12 (d, J=7.5, 1-β-CH₃); 1.33 (d, J=7.5, CH₃—CHOH); 3.38 (d,d J=3, J=7, C-6H); 3.45 (m, C-1H); 4.31 (m, CH₃CHOH); 4.2 (d,d J=3, J=10.5 C-5H); 4.7 (s, CH₂OH); 5.18 (ABq, ArCH₂O); 7.12–8.05 (m, ArH).

EXAMPLE 8

1. Preparation of 2-Methoxymethylfluoren-9-on-6-ylboronic Acid by solvolysis/ketalization protection steps followed by metallation/borylation.

A. Solvolysis and ketalization Reactions

Preparation of 6-Bromo-2-methoxymethyl-9-fluorenone Dimethyl Ketal

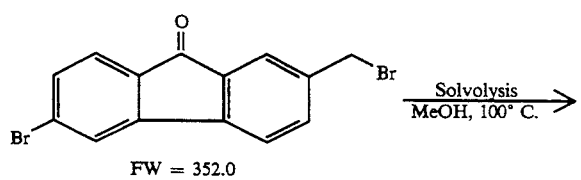

FW = 352.0

Solvolysis
MeOH, 100° C.

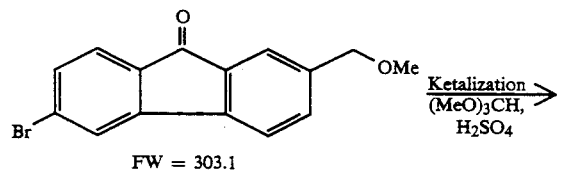

FW = 303.1

Ketalization
(MeO)$_3$CH,
H$_2$SO$_4$

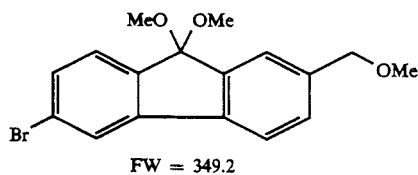

FW = 349.2

Part a - (conversion of benzylic bromide to methyl ether)

Absolute methyl alcohol (200 mL; 10 mL/g) was charged to a dry glass-lined pressure-rated (to 100 psi) vessel equipped with a mechanical stirrer under a N$_2$ atmosphere. 6-Bromo 2-bromomethyl 9-fluorenon (20 g; 0.057 mol) was charged and the resulting slurry was heated at 100° C. in the sealed vessel for 24 hours. The mixture was cooled to room temperature. The methyl ether crystallized upon cooling.

Ketalization of the carbonyl

The reaction mixture from Part 4a was cooled to 0°–5° C. and sequentially charged with concentrated sulfuric acid (4.6 mL; added dropwise to prevent splattering, exothermic) and trimethyl orthoformate (93.5 mL, 0.855 mol; slightly endothermic). The reaction flask was fitted with a distillation head and the reaction mixture was heated and distillate was collected (~60 mL) until the internal temperature reached 60° C. (still head temperature: 55° C.). The reaction mixture was then heated at 60° C. under reflux for 1.5 hours. The colorless to pale yellow solution was cooled to 10° C. Triethylamine (47.7 mL, 34.6 g, 0.34 mol; 4 mol/mol of H$_2$SO$_4$; KF≦100 μg/mL) was added to the stirred mixture. The solution was taken to a minimum volume (~57 mL) by distillation in vacuo (internal temperature ≦30° C.). The mixture was diluted with toluene (400 mL) and aqueous NaOH solution (400 mL, 1.0N) and agitated. The phases (both cloudy) were separated and the aqueous phase was extracted with toluene (200 mL). The combined organic phases were washed twice with D.I. water (200 mL). The organic phase was filtered into the next reaction vessel (suitable for cryogenic reactions) (clear solution at this point) and azeotropically dried by vacuum distillation of toluene (internal temperature ≦53° C.) to a KF ≦100 μg/mL. The solution was reduced to a minimum volume (57 mL) prior to the next reaction.

B. Metallation/Boronation

Preparation of 2-Methoxymethylfluoren 9-on-6-ylboronic Acid

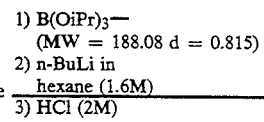

MW = 349.22

1) B(OiPr)$_3$—
(MW = 188.08 d = 0.815)
2) n-BuLi in hexane (1.6M)
3) HCl (2M)

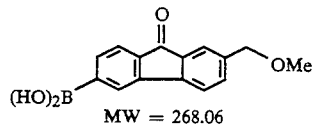

MW = 268.06

Into a dry three liter three necked round bottom flask equipped with a 500 mL addition funnel, thermocouple probe, and nitrogen inlet, were charged the solution of ketal in toluene (420 mL, 1.07M) and tetrahydrofuran (1.7 L, KF<44 μg/mL) at room temperature. The air in the reaction flask was exchanged by three vacuum purges with nitrogen. A sample is taken to verify a KF<100 μg/mL. Triisopropyl borate (150 mL, 651 mmol) was added to the solution at room temperature. The mixture was cooled to −78° C. and n-butyl lithium solution (1.6M in hexanes; 395 mL; 628 mmol) was slowly added over 3 hours, maintaining the temperature at −80° to −75° C. After 30 minutes, an aliquot of the reaction mixture was taken and quenched into acetic acid for HPLC assay. Typically, 2.0 area % of the bromo compound remained. Additional n-butyl lithium solution (1.6M; 19 mL; 30.4 mmol) was added to the reaction mixture over 10 minutes at −80° to −75° C. After aging for 20 minutes, a reaction aliquot was assayed by HPLC. In a typical case, 0.1 area % of the bromo compound remained. The reaction mixture was allowed to warmed to 20° C. over 1 hour. To the solution was added aqueous sulfuric acid (2M; 920 mL; 1.84 mol) over 10 minutes. The reaction temperature rose to 28° C. The mixture was vigorously stirred for 30 minutes. The organic layer (2.62 L) was separated. The aqueous layer (1.2 L) was extracted with ethyl acetate (0.5 L and 0.2 L). The combined organic extracts were concentrated to 300 mL under 165 mm bar (38° C. bath). The product crystallized out. To this mixture was added DI water (450 mL), and the resulting three phase mixture was stirred overnight at room temperature. The precipitates were collected on a 600 mL sintered glass filtered, washed with toluene (100 mL) and DI water (3×150 mL), and dried under house vacuum (nitrogen sweep) at 80° C. overnight (filter cake; 9.8 cm ID×2.5 cm). 2-Methoxymethylfluoren-9-one-6-boric acid was obtained as a mono-hydrate (125.8 g, 91.1 wt % purity) in 95.2% corrected yield.

2. Preparation of 5-cyano-4'-hydroxyoxymethyl-biphenyl-3-boronic acid

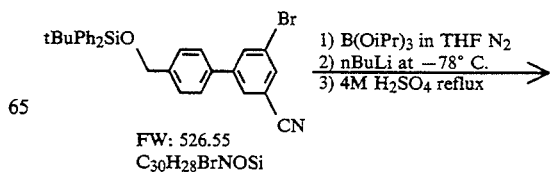

FW: 526.55
C$_{30}$H$_{28}$BrNOSi

1) B(OiPr)$_3$ in THF N$_2$
2) nBuLi at −78° C.
3) 4M H$_2$SO$_4$ reflux

-continued

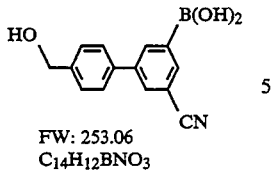

FW: 253.06
C₁₄H₁₂BNO₃

To 1-bromo-4-tert-butyldiphenylsilyloxymethylbenzene (1.224 Kg; 2.32 mol) was added dry (KF<50 µg/mL) THF (10.5 L) and B(OiPr)₃ (794 mL; 3.44 mol; 1.48 eq) at room temperature under nitrogen. The air in the reaction flask was completely exchanged by three vacuum purges with nitrogen. A sample is taken to verify a KF<100 µg/mL. The solution was cooled down to −78° C. To the solution was added 1.6M solution of n-BuLi in hexanes (2.08 L; 3.32 mol; 1.43 eq) at −78° to −75° C. over 2 hours. The mixture was allowed to warm up to 17° C. To the mixture was added 4M H₂SO₄ (4.64 L) at 5° C. The reaction was slightly exothermic and the temperature rose to 10° C. The reaction mixture was refluxing for 48 hours.

After cooling down to room temperature, 5M aqueous potassium hydroxide (7.7 L) was dropwise added to the mixture below 20° C. (pH was about 10.8). During neutralization, inorganic salt (K₂SO₄) was precipitated. To this mixture was added 1M aqueous potassium hydroxide (2.23 L) below 20° C. (pH was about 12.5). To this mixture was added t-butylmethyl ether (5 L) and stirred at room temperature for 30 minutes. The aqueous layer was separated and THF (2.5 L) was added to the aqueous solution. The aqueous solution was adjusted it pH to 2.7 with conc. HCl (about 374 mL) below 20° C. The mixture was extracted after stirring with ethyl acetate (5 L), dried over MgSO₄ (about 200 g), and concentrated in vacuo. The residual solid was dissolved in DMF (2.3 L) at 100° C. and added DI water (6.9 L) at 100° C. The mixture was cooled down to room temperature gently and aged at ambient temperature overnight. The crystals were collected by filtration, washed with 30% cold aqueous DMF (2 L) and then DI water (2 L), and dried in over at room temperature overnight to give 524 g of the desired boronic acid.

What is claimed is:

1. A compound of Formula

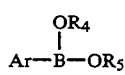

wherein
Ar is

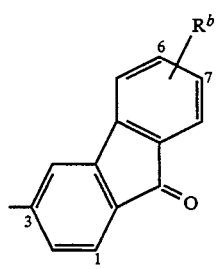

$R^b$ is
  (a) $C_{1-3}$ alkyl,
  (b) $C_{1-3}$ alkoxy,
  (c) substituted $C_{1-3}$ alkyl, wherein the substituent is hydroxy, or
  (d) hydroxy $C_{1-3}$ alkyl, wherein the hydroxy is optionally protected with a silyl protecting group selected from tri-$C_{1-4}$ alkyl silyl, phenyl di $C_{1-4}$ alkyl and diphenyl mono $C_{1-4}$ alkyl silyl;

$R^c$ is
  (a) $C_{1-3}$ alkyl,
  (b) hydroxy $C_{1-3}$ alkyl, wherein the hydroxy is optionally protected with a silyl protecting group selected from tri-$C_{1-4}$ alkyl silyl, phenyl di $C_{1-4}$ alkyl and diphenyl mono $C_{1-4}$ alkyl silyl;
  and wherein R₄ and R₅ are each individually hydrogen or $C_{1-6}$ alkyl or R₄ and R₅ are taken together are $C_{1-6}$ alkyl.

2. A compound according to claim 1 wherein $R^b$ and $R^c$ are each —CH₂OH—OCH₃, —CH₃ or triethylsilyl wherein $R^b$ resides at position 6 or 7 of the fluorenone and $R^c$ resides at position 4 of the phenyl.

3. A compound of Formula

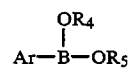

wherein
Ar is

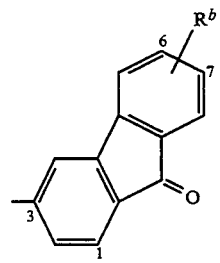

$R^b$ is
  (a) $C_{1-3}$ alkyl,
  (b) $C_{1-3}$ alkoxy,
  (c) substituted $C_{1-3}$ alkyl, wherein the substituent is hydroxy, or
  (d) hydroxy $C_{1-3}$ alkyl, wherein the hydroxy is protected with a silyl protecting group selected from tri-$C_{1-4}$ alkyl silyl, phenyl di $C_{1-4}$ alkyl and diphenyl mono $C_{1-4}$ alkyl silyl;
  and wherein R₄ and R₅ are each individually hydrogen or $C_{1-6}$ alkyl or R₄ and R₅ are taken together are $C_{1-6}$ alkyl.

4. A compound according to claim 3 wherein $R^b$ is —CH₂OH, —OCH₃, —CH₃ or triethylsilyl wherein $R^b$ resides at position 6 or 7 of the fluorenone.

* * * * *